United States Patent [19]

Balakirev et al.

[11] 4,119,661
[45] Oct. 10, 1978

[54] PROCESS FOR PRODUCING ALKALI SALTS OF ALKYLSULPHONIC ACIDS

[76] Inventors: Efim Stepanovich Balakirev, ulitsa akademika Skryabina, 30, korpus 2, kv. 43; Galina Ilinichna Bogomolova, ulitsa Novo-Ostapovskaya, 8, kv. 69; Abram Iosifovich Gershenovich, ulitsa M.Ulyanovoi, 16, kv. 124; Irina Viktorovna Gruzdeva, ulitsa Tikhomirova, 7, korpus 3, kv. 121, all of Moscow, U.S.S.R.

[21] Appl. No.: 783,027

[22] Filed: Mar. 30, 1977

[30] Foreign Application Priority Data

Apr. 5, 1976 [SU] U.S.S.R. .............................. 2343735

[51] Int. Cl.$^2$ ........................................... C07C 143/02
[52] U.S. Cl. ................................................. 260/513 R
[58] Field of Search ................................... 260/513 R

[56] References Cited

U.S. PATENT DOCUMENTS

| | | | |
|---|---|---|---|
| 3,507,909 | 4/1970 | Blackwell | 260/513 R |
| 3,577,456 | 5/1971 | Kleiner et al. | 260/513 R |
| 3,926,757 | 12/1975 | Rosinger | 260/513 R |

*Primary Examiner*—Nicky Chan
*Attorney, Agent, or Firm*—Lackenbach, Lilling & Siegel

[57] ABSTRACT

A process for producing alkali salts of alkylsulphonic acids, wherein the alkyl contains 11 to 18 carbon atoms which comprises outgassing the reaction mixture resulting from sulphoxidation of n-paraffins, having from 11 to 18 carbon atoms, taken either separately or in various combinations and consisting of corresponding alkylsulphonic acids, sulphuric acid, unreacted n-paraffins, sulphurous anhydride and water; the outgassed reaction mixture is neutralized with an aqueous solution of an alkali; the neutralizate is maintained at a temperature of from 100 to 160° C under a gauge pressure of from 1 to 6 atmospheres to allow stratification into two layers: the upper layer comprising the unreacted n-paraffins, the lower layer comprising an aqueous solution of a mixture of alkali salts of corresponding alkylsulphonic acids and alkali salts of sulphuric acid; the upper layer is separated and the lower layer is added with aliphatic saturated monohydric $C_1$-$C_4$ alcohols (weight ratio between the lower layer and the alcohol is 1:1-2); the resulting aqueous alcoholic solution of the alkali salts is maintained at a temperature of from 2 to 20° C to precipitate the alkali salts of sulphuric acid; the precipitate is separated from the aqueous alcoholic solution of alkali salts of corresponding alkylsulphonic acids; the solution is evaporated. The resulting desired products contain a minor amount of mineral impurities (below 1 wt.% of solids) and are efficient emulsifiers adapted for use in polymerization processes.

4 Claims, No Drawings

PROCESS FOR PRODUCING ALKALI SALTS OF ALKYLSULPHONIC ACIDS

FIELD OF THE INVENTION

The present invention relates to processes for producing alkali salts of alkylsulphonic acids useful as emulsifying agents in polymerization processes and for the manufacture of synthetic detergents.

BACKGROUND OF THE INVENTION

Known in the art are processes for producing alkali salts of alkylsulphonic acids, wherein the alkyl contains 10 to 20 carbon atoms, comprising outgassing the reaction mixture obtained from sulphoxidation of n-paraffins having from 10 to 20 carbon atoms, taken either separately or in various combinations and consisting of corresponding alkylsulphonic acids, sulphuric acid, unreacted n-paraffins, sulphurous anhydride and water. Thereafter the outgassed reaction mixture is added either with aliphatic saturated monohydric alcohols having from 1 to 5 carbon atoms, or an alcoholic solution of an alkali.

In the former case (addition of alcohols) the resulting mixture is stratified into two layers, the upper layer comprising the unreacted n-paraffins contaminated with the alcohol and the lower layer comprising an aqueous-alcoholic solution of corresponding alkylsulphonic acids and sulphuric acid.

In the latter case (addition of an alcoholic solution of an alkali) the resulting mixture is stratified into three layers: the upper one comprises the unreacted n-paraffins contaminated with the alcohol; the middle layer is an aqueous-alcoholic solution of alkali salts of corresponding alkylsulphonic acids; the lower layer comprises an aqueous solution of alkali salts of sulphuric acid.

In the former case the lower layer is separated from the upper layer of the unreacted n-paraffins and neutralized with an aqueous alkali solution. The resulting neutralizate is, in turn, stratified into two layers, the upper one comprising an aqueous alcoholic solution of alkali salts of corresponding alkylsulphonic acids and the lower layer - an aqueous solution of alkali salts of sulphuric acid. The lower layer is separated from the upper layer, whereafter the desired product is recovered from the remaining upper layer in the form of a paste or a melt (i.e. in a molten condition) by means of evaporation or salting-out with a saturated solution of sodium chloride.

In the latter case the middle and lower layers are separated from the upper layer of the unreacted n-paraffins, whereafter operations similar to those of the former case are performed.

The alkali salts of alkylsulphonic acids prepared by conventional processes feature a high content of alkali salts of sulphuric acid (mineral impurities) within the range of from 4 to 16% by weight as calculated for solids.

Presence of mineral impurities in alkali salts of alkylsulphonic acids in increased amounts makes it impossible to utilize them as emulsifying agents in polymerization processes.

These prior art processes also have a disadvantage residing in that the recovered n-paraffins are contaminated with alcohol. Those n-paraffins cannot be recycled to the stage of sulphoxidation without resorting to purification thereof from the alcohol.

BRIEF SUMMARY OF THE INVENTION

It is an object of the present invention to provide a process for producing alkali salts of alkylsulphonic acids which would enable the production of the desired products with a low content of mineral impurities.

It is another object of the present invention to provide a process for producing alkali salts of alkylsulphonic acids which would make it possible to recover the unreacted paraffins without being contaminated with alcohol.

These and other objects of the present invention are accomplished by a process for producing alkali salts of alkylsulphonic acids, wherein the alkyl contains 11 to 18 carbon atoms which comprises out-gassing a reaction mixture resulting from sulphoxidation of n-paraffins with from 11 to 18 carbon atoms, taken either separately or in various combinations and consisting of corresponding alkylsulphonic acids, sulphuric acid, unreacted n-paraffins, sulphurous anhydride and water, whereafter the outgassed reaction mixture in accordance with the present invention is neutralized with an aqueous solution of an alkali at a temperature of from 40° to 95° C. to give a neutralizate consisting of alkali salts of corresponding alkylsulphonic acids, alkali salts of sulphuric acid, unreacted n-paraffins and water. Thereafter the neutralizate is maintained at a temperature within the range of from 100° to 160° C., preferably from 120° to 140° C. under a gauge pressure of from 1 to 6 atmospheres, preferably from 2 to 3.5 atmospheres to separate the neutralizate into two layers. The upper layer comprises the unreacted n-paraffins, the lower one — an aqueous solution of a mixture of alkali salts of corresponding alkylsulphonic acids and alkali salts of sulphuric acid. The upper layer is separated while the lower layer is added with aliphatic saturated monohydric alcohols containing 1 to 4 carbon atoms at a weight ratio between the lower layer and the alcohol equal to 1:1–2 respectively. The resulting aqueous alcoholic solution of the mixture of alkali salts of corresponding alkylsulphonic acids and alkali salts of sulphuric acids is maintained at a temperature within the range of from 2° to 20° C. Alkali salts of sulphuric acids are then precipitated in the form of crystals which are separated from the aqueous-alcoholic solution of the alkali salts of corresponding alkylsulphonic acids and said aqueous-alcoholic solution is evaporated.

It is advisable that the separated upper layer comprising the unreacted n-paraffins be recycled back into the sulphoxidation process; this requires no preliminary purification of the n-paraffins.

The process according to the present invention makes it possible to produce the desired products with a low content of mineral impurities (below 1% by weight as calculated for solids). These products can be effectively used as emulsifying agents in polymerization processes. The desired products have a light-yellow color or are colorless.

Besides, the process according to the present invention makes it possible to recover the unreacted n-paraffins un-contaminated with alcohol. Such n-paraffins can be recycled, as it has been mentioned hereinbefore, back into the sulphoxidation process without any additional treatment.

DETAILED DESCRIPTION OF THE INVENTION

The starting reaction mixture employed in the process of the present invention is obtained by a conventional method involving sulphoxidation of n-paraffins under irradiation with UV-light, γ-rays or in the presence of radical-type initiators.

Outgassing of the starting reaction mixture is performed by conventional techniques such as purging of sulphurous anhydride with an inert gas, air or oxygen; heating of the reaction mixture to a temperature of from 50° to 60° C. under vacuum.

In the neutralization stage of the inventive process use may be made of aqueous alkali solutions such as sodium hydroxide, potassium hydroxide and lithium hydroxide.

Prior to evaporation of the aqueous-alcoholic solution of alkali salts of alkylsulphonic acids it is possible to carry out extraction of the dissolved n-paraffins with a low-boiling solvent such as gasoline or n-pentane, petroleum ether.

Evaporation of the aqueous-alcoholic solution of alkali salts of alkylsulphonic acids is conducted until the desired products are obtained in the form of a melt (i.e. in a molten condition) or, in the case of preliminary extraction of the contaminating n-paraffins, in the form of a paste.

The desired products can be used in the form of a paste (in the case of a melt, it is added with water to a required concentration) or in the form of solid flakes obtained by crystallization of a melt in a cooled roll mill.

For a better understanding of the present invention the following examples illustrating its embodiments are given hereinbelow.

EXAMPLE 1

A reaction mixture resulting from sulphoxidation of n-paraffins containing 11 to 18 carbon atoms by irradiation with UV-light in the presence of water and consisting of 21.3% by weight of corresponding alkylsulphonic acids, 6.7% by weight of sulphuric acid, 24.5% by weight of unreacted n-paraffins, 2.7% by weight of sulphurous anhydride and 44.8% by weight of water is outgassed by air-purging. To 500 g of the outgassed reaction mixture consisting of 22.2% by weight of alkylsulphonic acids, 7% by weight of sulphuric acid, 25.6% by weight of unreacted n-paraffins, 45.2% by weight of water, there are added 107 g of a 42% aqueous solution of sodium hydroxide at a temperature of 90° C. and the mixture is stirred for 30 minutes. The resulting neutralizate is heated in an autoclave to 140° C. under a gauge pressure of 3 atmospheres. After 1 hour of residence under said pressure and temperature, the neutralizate is stratified into two layers. The neutralizate is then cooled to 30° C. The upper layer comprising the unreacted n-paraffins is separated in the amount of 105 g. The remaining lower layer of the neutralizate is added, under stirring, with 500 g of propanol (weight ratio of the lower layer to the alcohol is 1:1). The thus-prepared aqueous-alcoholic solution is maintained at 10° C. for 30 minutes. Therewith, sodium sulphate is precipitated in the form of crystals which are then separated by filtration. From the filtrate (aqueous-alcoholic solution) n-paraffins are extracted with petroleum ether. The aqueous-alcoholic solution after extraction of n-paraffins is evaporated to give 186 g of a paste of sodium salts of alkylsulphonic acids of the following composition, percent by weight:

sodium salts of alkylsulphonic acids — 60.7
sodium sulphate — 0.4
n-paraffins — 0.2
water — 38.7

EXAMPLE 2

To 500 g of an outgassed reaction mixture prepared in a manner similar to that described in the foregoing Example 1 and containing the same components there are added 107 g of a 42% aqueous solution of sodium hydroxide at a temperature of 160° C. under a gauge pressure of 6 atmospheres. After residence of the neutralizate for 1 hour under the above-mentioned conditions, the neutralizate is stratified into two layers. Then the neutralizate is cooled to 30° C. The upper layer comprising the unreacted n-paraffins is separated in the amount of 108 g. The remaining lower layer of the neutralizate is added, under stirring, with 1,000 g of 85% propanol (weight ratio of the lower layer to the alcohol is 1:2). The resulting aqueous-alcoholic solution is maintained at a temperature of 10° C. for 30 minutes. The precipitated, as crystals, sodium sulphate is separated by filtration. The filtrate comprising an aqueous alcoholic solution of sodium salts of alkylsulphonic acids with impurities of sodium sulphate and n-paraffins is evaporated at a temperature of 180° C. under a pressure of 10 atm to the condition of a melt. The latter is diluted with water to give 188 g of a paste of the following composition, percent by weight:

sodium salts of alkylsulphonic acids — 59.1
sodium sulphate — 0.32
n-paraffins — 0.28
water — 40.3

EXAMPLE 3

A reaction mixture resulting from sulphoxidation of n-paraffins having from 11 to 18 carbon atoms and consisting of 25.4% by weight of corresponding alkyl-sulphonic acids, 8.0% by weight of sulphuric acid, 27.6% by weight of unreacted n-paraffins, 2.3% by weight of sulphurous anhydride and 36.7% by weight of water is outgassed by heating to a temperature of 50° C. under vacuum (200 mm Hg). To 500 g of the outgassed reaction mixture consisting of 27.4% by weight of alkylsulphonic acids, 8.7% by weight of sulphuric acid, 29.8% by weight of the unreacted n-paraffins and 34.1% by weight of water, there are added 135 g of a 42% aqueous solution of sodium hydroxide at a temperature of 90° C. under stirring. The resulting neutralizate is heated in an autoclave 150° C. under a gauge pressure of 4.5 atmospheres. After 80 minutes of residence under the above-mentioned conditions the neutralizate is stratified into two layers. Thereafter, the neutralizate is cooled to 25° C. The upper layer comprising the unreacted n-paraffins is separated in the amount of 120 g. The remaining lower layer of the neutralizate is added under stirring with 780 g of ethanol (weight ratio between the lower layer and ethanol is 1:1.5). The resulting aqueous-alcoholic solution is maintained at the temperature of 3° C. for 40 minutes. Therewith, sodium sulphate is precipitated as crystals which are then separated by centrifugation. From the filtrate (aqueous-alcoholic solution) the contaminant n-paraffins are extracted with petroleum ether. The aqueous-alcoholic solution after extraction of n-paraffins is evaporated to give 220 g of a paste of sodium salts of the following composition, percent by weight:
sodium salts of alkylsulphonic acids — 62.3
sodium sulphate — 0.2
n-paraffins — 0.4
water — 37.1

EXAMPLE 4

500 g of an outgassed reaction mixture prepared in a manner similar to that described in the foregoing Example 3 and having the same composition as in that Example, are neutralized by addition of 188 g of a 42% aqueous solution of potassium hydroxide at a temperature of 50° C. Treatment of the neutralizate and subsequent operations are performed in a manner similar to that described in Example 3. As a result, 244 g of a paste of potassium salts of alkylsulphonic acids are obtained having the following composition, percent by weight:
potassium salts of alkylsulphonic acids — 59
potassium sulphate — 0.35
n-paraffins — 0.55
water — 40.1

EXAMPLE 5

To 500 g of an outgassed reaction mixture prepared by a procedure similar to that described in the foregoing Example 1 and having the same composition there are added 150 g of a 30% aqueous solution of sodium hydroxide at a temperature of 90° C. under stirring. The resulting neutralizate is heated in an autoclave to a temperature of 120° C. under the pressure and kept under these conditions for 2 hours. Therewith, the neutralizate is stratified into two layers. After cooling the neutralizate, the upper layer comprising the unreacted n-paraffins is separated in the amount of 100 g. The lower layer comprising an aqueous solution of sodium salts of corresponding alkylsulphonic acids, sodium sulphate and contaminating n-paraffins is added under stirring with 500 g of methanol (weight ratio of the lower layer to the alcohol is 1:1). The resulting aquo-alcoholic solution is maintained at a temperature of 20° C. for 40 minutes. The precipitated sodium sulphate is separated by filtration and the contaminant of n-paraffins is extracted from the filtrate (aqueous-alcoholic solution) by means of n-pentane. After the extraction, the aqueous-alcoholic solution is evaporated to give 183 g of a paste of sodium salts of alkylsulphonic acids of the following composition, percent by weight:
sodium salts of alkylsulphonic acids — 60.7
sodium sulphate — 0.3
n-paraffins — 0.5
water — 38.5

EXAMPLE 6

A reaction mixture prepared by sulphoxidation of n-tetradecane upon initiation by means of γ-rays in the presence of water and consisting of 23.5% by weight of tetradecane sulphonic acid, 7.4% by weight of sulphuric acid, 20.4% by weight of n-tetradecane, 2.8% by weight of sulphurous anhydride and 45.9% by weight of water is outgassed by purging with oxygen. To 500 g of the outgassed reaction mixture consisting of 24.6% by weight of tetradecane sulphonic acid, 7.7% by weight of sulphuric acid, 21.3% by weight of the unreacted n-tetradecane and 46.4% by weight of water there is added under stirring and at a temperature of 70° C. 120 g of a 42% aqueous solution of sodium hydroxide. The resulting neutralizate is heated in an autoclave at a temperature of 160° C. under a gauge pressure of 6 atmospheres. After 30 minutes of residence under said conditions the neutralizate is stratified into two layers. The upper layer comprising the unreacted n-tetradecane is separated in the amount of 97 g. To the remaining lower layer of the neutralizate there is added under stirring 520 g of isopropanol (weight ratio between the lower layer and the alcohol is 1:1). The resulting aqueous-alcoholic solution is maintained at a temperature of 5° C. for 60 minutes. Therewith, sodium sulphate is precipitated in the form of crystals which are separated by filtration. The contaminating n-tetradecane is extracted from the filtrate (aqueous-alcoholic solution) by means of petroleum ether. The aqueous-alcoholic solution after said extraction is evaporated to give 220 g of a paste having the following composition, percent by weight:
sodium salt of tetradecane sulphonic acid — 57.7
sodium sulphate — 0.30
n-tetradecane — 0.1
water — 41.9

EXAMPLE 7

The reaction mixture prepared by sulphoxidation of n-paraffins with a number of carbon atoms of from 15 to 18 and consisting of 22.6% by weight of corresponding alkylsulphonic acids, 6.2% by weight of sulphuric acid, 24.3% by weight of the unreacted n-paraffins, 2.4% by weight of sulphurous anhydride and 44.5% by weight of water is outgassed by purging with air. To 500 g of the outgassed reaction mixture consisting of 23.4% by weight of alkylsulphonic acids, 6.4% by weight of sulphuric acid, 25.2% by weight of the unreacted n-paraffins and 45% by weight of water, there are added 111 g of a 42% aqueous solution of sodium hydroxide at a temperature of 40° C. under stirring. The resulting neutralizate is heated in an autoclave to a temperature of 100° C. under a gauge pressure of 1 atmospheres. After 3 hours of residence in the autoclave under the above mentioned conditions the neutralizate is stratified into two layers. The neutralizate is then cooled to a temperature of 30° C. The upper layer (the unreacted n-paraffins) in the amount of 104 g is separated and the lower layer is added, under stirring, with 1,000 g of ethanol (weight ratio of the lower layer to the alcohol is 1:2). The resulting aquo-ethanolic solution is maintained at a temperature of 20° C. for 60 minutes. The precipitated crystals of sodium sulphate are separated by centrifugation. The contaminant of n-paraffins is extracted from the filtrate (aqueous-ethanolic solution) by means of petroleum ether and then evaporated to give 235 g of a paste of sodium salts of corresponding alkylsulphonic acids of the following composition, percent by weight:
sodium salts of alkylsulphonic acids — 61.7
sodium sulphate — 0.55
n-paraffins — 0.35
water — 37.4

What is claimed is:

1. A process for producing alkali metal salts of alkylsulfonic acids, wherein the alkyl contains 11 to 18 carbon atoms, comprising sulfoxidation of n-paraffins selected from the group consisting of 11 to 18 carbon atoms, and mixtures thereof; to form a reaction mixture which includes the corresponding alkylsulfonic acids, sulfuric acid, unreacted n-paraffins, sulfurous anhydride and water; outgassing said reaction mixture; neutralizing the outgassed reaction mixture with an aqueous solution of alkali metal hydroxides at a temperature of from 40°–95° C. to form an alkali metal salt neutralization product; maintaining the neutralization product at a temperature of from 100° to 160° C. under a gauge pressure of from 1 to 6 atmospheres to stratify the neutralization product into two layers, the upper layer comprising unreacted n-paraffins, the lower layer comprising an aqueous solution of a mixture of alkali metal salts of corresponding alkylsulfonic acids and sulfuric acid; separating the upper layer; adding saturated aliphatic $C_1$ to $C_4$ monohydric alcohols so that the weight ratio of lower layer to alcohol equals 1:1–2 respectively, to form an aqueous alcohol solution containing alkali metal salts of the corresponding alkylsulfonic acids and sulfuric acid; maintaining the resulting aqueous alcohol salt solution of said acids at a temperature of from 2° to 20° C. to precipitate the alkali metal salts of sulfuric acid; separating the precipitate from the aqueous alcohol solution of alkali salts of the corresponding alkylsulfonic acids; and recovering said alkylsulfonic acids.

2. A process as claimed in claim 1, wherein the neutralization product is maintained at a temperature of from 120° to 140° C. under a gauge pressure of from 2.0 to 3.5 atmospheres.

3. A process as claimed in claim 1, wherein the separated upper layer comprising the unreacted n-paraffins is recycled into the process of sulphoxidation.

4. The process of claim 1, wherein said alkylsulfonic acid is recovered by evaporation of the aqueous alcohol solution.

* * * * *